United States Patent [19]

Hayase et al.

[11] Patent Number: 4,695,312
[45] Date of Patent: Sep. 22, 1987

[54] 4,5,6,7-TETRAHYDRO-2H-INDAZOLE DERIVATIVES AND HERBICIDES CONTAINING THEM

[75] Inventors: Yoshio Hayase, Mie; Toshikazu Ohtsuka; Kinya Ide, both of Shiga; Toshio Takahashi, Hyogo, all of Japan

[73] Assignee: Shionogi & Co., Ltd., Osaka, Japan

[21] Appl. No.: 846,051

[22] Filed: Mar. 31, 1986

[30] Foreign Application Priority Data

Apr. 3, 1985 [JP] Japan .................................. 60-71428

[51] Int. Cl.$^4$ .................... A01N 43/56; C07D 231/56
[52] U.S. Cl. .......................................... 71/92; 548/369
[58] Field of Search ............................. 548/369; 71/92

[56] References Cited

U.S. PATENT DOCUMENTS 4,608,080 8/1986 Haga et al. .......................... 548/369

Primary Examiner—Henry R. Jiles
Assistant Examiner—Kurt G. Briscoe
Attorney, Agent, or Firm—Wenderoth, Lind & Ponack

[57] ABSTRACT

A compound (I) of the formula:

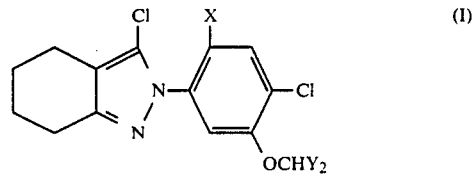

(wherein X and Y each is halogen) and herbicidal compositions containing the compound (I) are provided.

4 Claims, No Drawings

4,5,6,7-TETRAHYDRO-2H-INDAZOLE DERIVATIVES AND HERBICIDES CONTAINING THEM

BACKGROUND OF THE INVENTION

1. Field of the Invention

The present invention relates to 4,5,6,7-tetrahydro-2H-indazoles which show potent herbicidal activity.

2. Prior Art

Phenylindazole derivatives having herbicidal activities are described in U.S. Pat. No. 4,059,434. Furthermore, the compounds analogous to the phenylindazole derivatives are disclosed in EP Pat. No. 105,721.

BRIEF SUMMARY OF THE INVENTION

The present invention relates to the compounds of the formula (I):

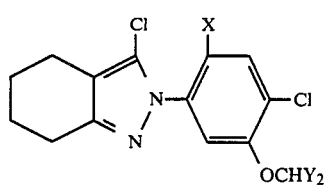

(wherein X and Y each is halogen); and it relates to a herbicidal composition comprising the compound of the formula (I) together with one or more carriers, diluents and/or excipients.

DETAILED DESCRIPTION OF THE INVENTION

The present invention relates to 2H-indazoles which show herbicidal activity.

More particularly, it relates to the compounds of the formula (I):

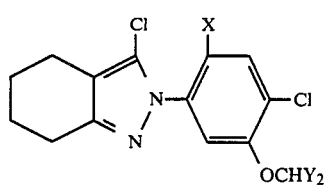

(wherein X and Y each is halogen) and acid addition salts thereof.

The compounds (I) can be prepared according to the following step.

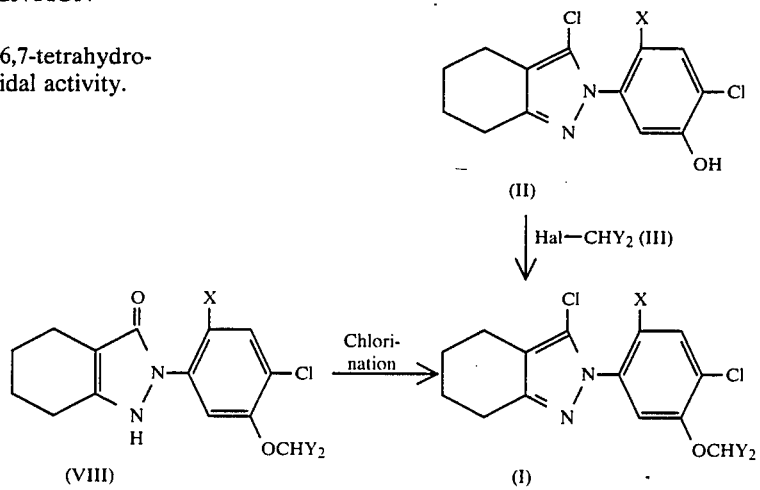

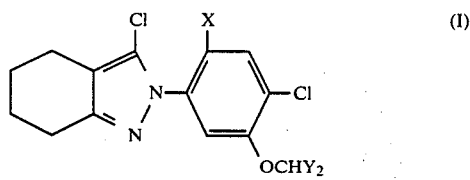

(wherein X and Y each has the same meaning as defined above; Hal is chlorine, bromine, or iodine; with the proviso that the halogen in Y has always a higher electronegativity than the halogen in Hal.

A mixture of a 3-chloro-2-(4-chloro-2-halo-5-hydroxyphenyl)-4,5,6,7-tetrahydro-2H-indazole derivative (II) and about 1 to 10 equimolar amounts of the compound (III) is allowed to react in an appropriate solvent at a temperature from room temperature to a temperature under heating, preferably at a temperature of about 50°~100° C. for about 1 to 10 hours to give the objective compound (I).

The solvent is exemplified by water, dioxane, acetonitrile, acetone, tetrahydrofuran, dimethylsulfoxide, methanol, isopropanol, dimethylformamide, and a mixture thereof. If required, a base may be used. When a water soluble solvent is used, an alkali metal hydroxide (e.g. sodium hydroxide, potassium hydroxide, etc.) can be used, and when a water insoluble solvent is used, an alkali metal hydride (e.g. sodium hydride, potassium hydride, etc.) can be employed.

Alternatively, 2-(4-chloro-5-dihalomethoxy-2-halophenyl)-1,2,4,5,6,7-hexahydro-3H-indazol-3-one (VIII) is chlorinated to give the objective compound (I). For chlorination, customary chlorinating agents such as phosphorus oxychloride, phosphorus trichloride, thionyl chloride, or phosgene can be used. The reaction may be performed at a temperature from room temperature to 160° C., if necessary in the presence of a solvent such as dichloromethane, dichloroethane, chloroform, carbon tetrachloride or the like.

The starting materials (II) are known or may be prepared as follows.

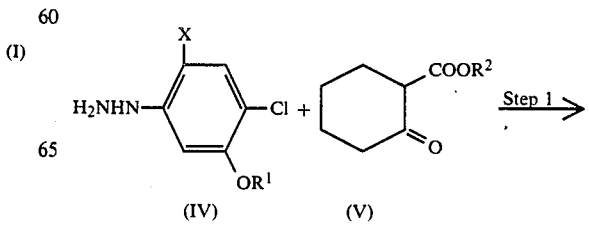

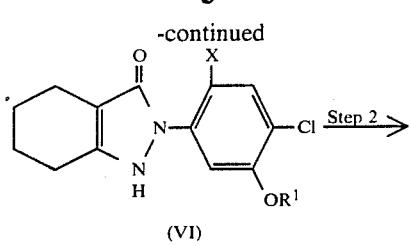

(VI)

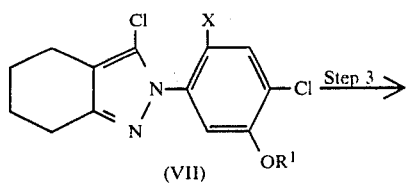

(VII)

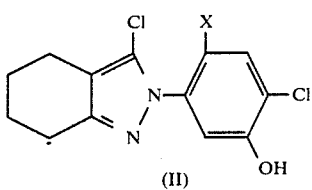

(II)

(wherein X has the same meaning as defined above; R¹ is hydroxy-protecting group such as lower alkyl, benzyl, benzoylmethyl, vinyl, trimethylsilyl, lower alkanoyl, benzoyl, lower alkoxycarbonyl, and the like; protecting groups are described in J. F. W. McOmie et al., Plenum Press London and New York (1973), pp. 145–182; and R² is lower alkyl).

The lower alkyl includes methyl, ethyl, n-propyl, isopropyl, n-butyl, sec-butyl, tert-butyl, n-pentyl, isopentyl, neo-pentyl, tert-pentyl, and the like.

Representatives of the lower alkanoyl are formyl, acetyl, pivaloyl, propionyl, valeryl, and the like.

The lower alkoxycarbonyl includes methoxycarbonyl, ethoxy-carbonyl, n-propoxycarbonyl, isopropoxycarbonyl, and the like.

Steps 1 to 3 for preparing the starting material (II) are explained below.

STEP 1

The indazolones (VI) can be prepared by reacting the hydrazine derivative (IV) or its acid addition salt (e.g. hydrochloride, etc.) with the 2-alkoxycarbonylcyclohexanone (V). The reaction may be carried out in an appropriate solvent, preferably in the presence of a base.

As the solvent, lower alkanols (e.g. methanol, ethanol, isopropanol, butanol, etc.); halogenohydrocarbons (e.g. dichloromethane, dichloroethane, chloroform, etc.); aromatic solvents (e.g. benzene, toluene, xylene, etc.) can be used.

As the base, organic bases such as triethylamine, N-methylmorpholine, piperidine, pyrrolidine, and the like can be employed.

The reaction can be carried out at a temperature from room temperature to a temperature under heating (e.g. 15°–120° C.) and terminates within a period of several hours to several ten hours.

STEP 2

In this step the indazole (VII) can be prepared by chlorinating the indazolone (VI), using a customary chlorinating agent such as phosphorus oxychloride, phosphorus trichloride, thionyl chloride, phosgene or the like. The reaction may be performed in a halogenohydrocarbon solvent as above illustrated at a temperature from room temperature to a temperature under heating. (e.g. 15°–160° C.)

STEP 3

The starting compound (II) is prepared by subjecting the indazole (VI) to deprotection. The reaction may be performed for preparing efficiently the starting compound (II) according to the properties of the protecting group R¹. For example, the reaction is performed in the presence of an acid such as hydrohalogenic acid (e.g. hydrochloric acid, hydroiodic acid, hydrobromic acid) or a boron halide such as boron trichloride or boron tribromide at a temperature under cooling to a temperature under heating (e.g. −80° to 120° C.). When R¹ is trimethylsilyl, alkanoyl, benzoyl or alkoxycarbonyl, the deprotection can be accomplished by treating VII with a base such as alkali hydroxide (e.g. sodium hydroxide, potassium hydroxide) in a solvent such as methanol, ethanol, dimethylsulfoxide, or dimethylformamide at 15° to 100° C.

Illustrating the case in which R¹ is isopropyl, the indazole (VII) is allowed to react with boron trichloride or boron tribromide in a solvent at a temperature under cooling to a temperature under heating (e.g. about −80° to 50° C.) for about 1 to 24 hours, whereby the compound (II) is obtained. The solvent includes illustratively halogenohydrocarbons such as dichloromethane, dichloroethane, chloroform or carbon tetrachloride and aromatic hydrocarbons such as benzene, toluene or xylene.

Further, another starting compound (VIII) can be prepared according to the following reaction scheme:

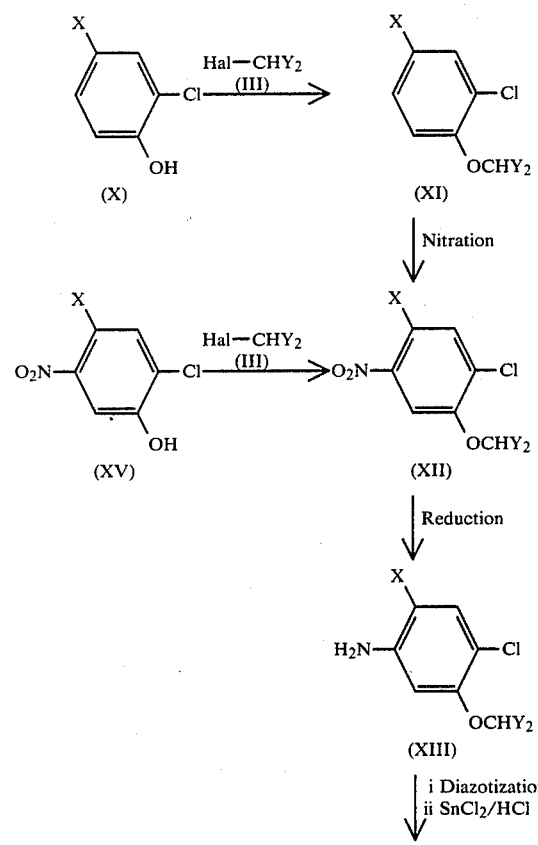

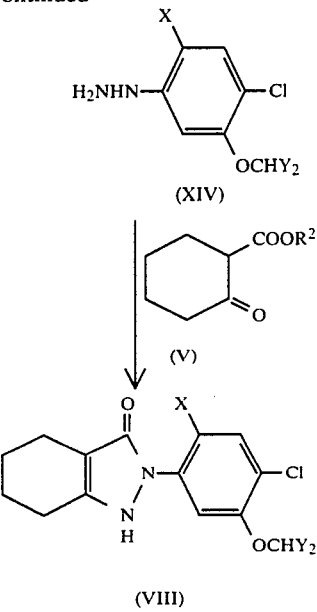

(wherein Hal, $R^2$, X and Y each is as defined above).

These reactions may be performed according to the reactions above described for the preparation of the starting compound (II) or in a conventional manner.

Appropriate application rate of the compound (I) of a present invention usable as a herbicidal ingredient is variable, depending upon the purpose of use, the kind of the objective grasses or weeds and the application period, and is generally 0.1 to 100 g/are, preferably 0.5 to 40 g/are. A compound (I) may be applied with or without dilution.

The herbicidal composition comprising a compound (I) of the present invention can be formulated in the form of agricultural preparations such as dusts, granules, emulsions, wettable powders, suspensions or solutions by admixing it with one or more solid or liquid carriers or combination thereof together with surfactants or other adjuvants. Appropriate effective ratio of a compound (I) of present invention in these preparations is 0.03 to 90% by weight, preferably 0.2 to 80% by weight.

The solid carriers include illustratively fine powders or granules such as clay (e.g. kaolin clay, attapulgite clay etc.), bentonite, acid clay, pyrophyllite, talc, diatomaceous earth, silicate earth, calcite, powder, urea, ammonium sulfate, amorphous hydrous silicon dioxide and the like. The liquid carriers include illustratively water, aromatic hydrocarbons such as benzene, toluene, xylene or methylnaphthalene, alcohols such as isopropanol, ethylene glycol, or cellosolve, ketones such as acetone, cyclohexanone or isophorone, vegetable oils such as soybean oil or cotton seed oil, dimethylsulfoxide, acetonitrile, cyclohexane and the like.

The surfactants include illustratively anionic surfactants such as alkylsulfuric ester, alkylarylsulfonate, dialkylsulfosuccinate, or polyoxyethylene alkyl aryl ether phosphate and nonionic surfactants such as polyoxyethylene alkyl aryl ether, polyoxyethylene polyoxypropylene block copolymer, sorbitan fatty acid ester or polyoxysorbitan fatty acid ester. The surfactants can work as an emulsifier, dispersant or wetting agent.

Other pharmaceutical adjuvants such as emulsifiers, stabilizers, dispersants, suspenders, spreaders, penetrants, wetting agents or the like may be added, and there are exemplified ligninsulfonate, arginate, polyvinyl alcohol, gum arabic, CMC (carboxymethyl cellulose), PAP (isopropyl hydrogenphosphate), polyoxyethylene resin acid (ester), abietate, and dinaphthylmethanedisulfonate in accordance with the purpose of the use.

These preparations are generally applied over the leaves and stalks or treated with soils, and in the case of soil treatment the preparations are applied over the surface of soils or irrigated in soils. The soils mean customary soils such as sandy loam or loamy soil, claycy soil and sandy soil.

Further, the elevation of the herbicidal potency and the expansion of the herbicidal spectrum can be expected by using them together with other herbicides such as diuron, alachlor, linuron, benthiocarb or the like. Moreover they may be admixed with known insecticides, miticides, nematocides, fungicides, plant growth regulators, manures, or soil improving agents.

Presently preferred and practical embodiments of the present invention are illustratively shown in the following Examples, Reference Examples and Formulations.

EXAMPLE 1

3-Chloro-2-(2,4-dichloro-5-difluoromethoxyphenyl)-4,5,6,7-tetrahydro-2H-indazole I-1

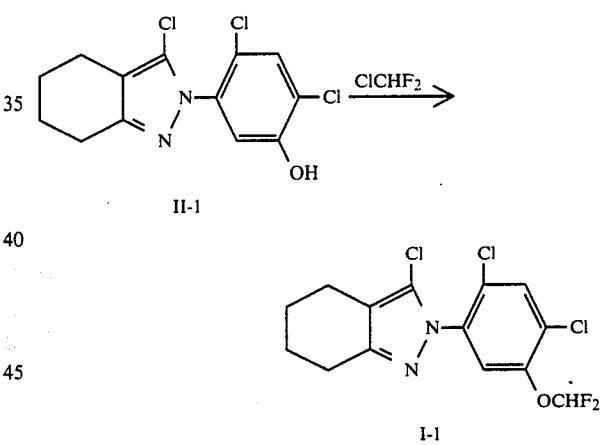

To a solution of 6.4 g of 3-chloro-2-(2,4-dichloro-5-hydroxyphenyl)-4,5,6,7-tetrahydro-2H-indazole II-1 in 12.5 ml of dioxane were added 12.5 ml of water and 6.4 g of 50% sodium hydroxide. The mixture was heated at 50°~60° C., mixed with excessive amount of chlorodifluoromethane, and heated at 50°~60° C. To the mixture was dropwise added 6.4 g of 50% sodium hydroxide respectively 2.5 hours later and 4 hours later within 15 minutes. The resulting mixture was allowed to react for 2.5 hours, cooled, neutralized, and extracted with ether. The extract was washed with saturated aqueous sodium chloride, dried and concentrated. The residue was purified by silica-gel chromatography to give 4.0 g of the titled compound I-1.

m.p.: 121°~123° C.

NMR (CDCl$_3$)δ (TMS as internal standard): 1.67–2.10(4H, m), 2.37–2.93(4H, m), 6.57(1H, t, J=72 Hz), 7.35(1H, s), 7.67(1H, s).

EXAMPLE 2

3-Chloro-2-(4-chloro-5-difluoromethoxy-2-fluorophenyl)-4,5,6,7-tetrahydro-2H-indazole I-2

To a solution of 36 ml of isopropanol, 21 ml of water and 6.0 ml of sodium hydroxide was added 5.28 g of 3-chloro-2-(4-chloro-2-fluoro-5-hydroxyphenyl)-4,5,6,7-tetrahydro-2H-indazole II-2, and the resultant mixture was heated at 50° to 60° C. to give a solution. Excessive chlorodifluoromethane gas was introduced, and each 4.5 g of 50% aqueous sodium hydroxide was added 1.5 and 3 hours after starting the gas inlet and further said gas inlet was continued for additional one hour. After cooling, the reaction mixture was neutralized with 2N hydrochloric acid and extracted with dichloromethane. The organic layer was dried and concentrated. The residue was chromatographed on a column of silica gel, eluting with n-hexane-ethyl acetate (4:1 v/v). The eluate was concentrated to give 5.24 g of the titled compound I-2.

m.p. 83°–85° C.

NMR (CDCl$_3$)δ (TMS as internal standard): 1.63–2.09(4H, m), 2.38–2.93(4H, m), 6.50(1H, t, J=70 Hz), 7.33(1H, d, J=9 Hz).

EXAMPLE 3

3-Chloro-2-(4-chloro-5-difluoromethoxy-2-fluoroyphenyl)-4,5,6,7-tetrahydro-2H-indazole I-2.

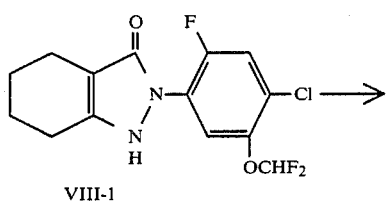

VIII-1

I-2

A mixture of 5.2 g of 2-(4-chloro-5-difluoromethoxy-2-fluorophenyl)-1,2,4,5,6,7-hexahydro-3H-indazol-3-one VIII-1 (containing a certain amount of its tautomer 2,3a,4,5,6,7-hexahydro compound) and 2.4 g of phosphorus oxychloride was stirred at 140° to 150° C. for 4 hours. After cooling, the resultant mixture was dissolved in chloroform, mixed with water and 4N sodium hydroxide and shaken with chloroform. The chloroform layer was dried and concentrated. The residue was chromatographed on a column of silica gel, eluting with n-hexane-ethyl acetate (20:1 v/v). The eluate was concentrated to give 2.65 g of the titled compound I-2.

m.p. 83°–85° C.

REFERENCE EXAMPLE 1

(1) 2-(2,4-Dichloro-5-isoproxyphenyl)-4,5,6,7-tetrahydro-2H-indazole VII-1

A mixture of 30 g of 2,4-dichloro-5-isopropoxyphenylhydrazine hydrochloride IV-1, 70 ml of ethanol, and 18.7 g of 2-ethoxycarbonylcyclohexanone was stirred at room temperature. To the mixture was dropwise added 22.4 g of triethylamine. The mixture was heated under reflux for 24 hours, cooled, mixed with 200 ml of water, and extracted. The extract was washed with water, dried, and concentrated to give 35.4 g of 2-(2,4-dichloro-5-isopropoxyphenyl)-1,2,4,5-6,7-hexahydro-3H-indazol-3-one VI-1 as a crude product.

A mixture of 19.2 g of the compound VI-1 provided above and 8.6 g of phosphorus oxychloride was heated under reflux for 6 hours. The reaction mixture was cooled, dissolved in 200 ml of chloroform, and mixed with 10% sodium hydroxide at 0° C. The chloroform layer was collected, washed with 10% sodium hydroxide, water and saturated brine in order, dried, and concentrated. The residue is purified by silica gel column chromatography to give 8.2 g of the titled compound VII-1.

Physical properties of the compound VII-1:

m.p.: 61°~63° C.

NMR (CDCl$_3$) δ (TMS as internal standard): 1.35(6H, d, J=7 Hz), 1.51–2.05(4H, m), 2.21–2.88(4H, m) 4.51(1H, septet, J=7 Hz), 6.96(1H, s), 7.46(1H, s).

(2) 2-(2,4-Dichloro-5-hydroxyphenyl)-4,5,6,7-tetrahydro-2H-indazole II-1

To a solution of 2.78 g boron tribromide in 5 ml of dichloromethane was added a solution of 3.10 g of 3-chloro-2-(2,4-dichloro-5-isopropoxyphenyl)-4,5,6,7-tetrahydro-2H-indazole VII-1 in 35 ml of dichloromethane under cooling at −78° C. in 15 minutes. The resultant mixture was stirred at −78° C. for 0.5 hours and at room temperature for 1.5 hours and mixed with water and ether at 0° C. The mixture was basified, and the aqueous layer was separated and acidified and shaken with ether. The extract was dried, concentrated and the residue was purified by silica gel chromatography, whereby 2.39 g of the titled compound II-1 was obtained.

m.p. 84°–86° C. Mass: M+ 316.

REFERENCE EXAMPLE 2

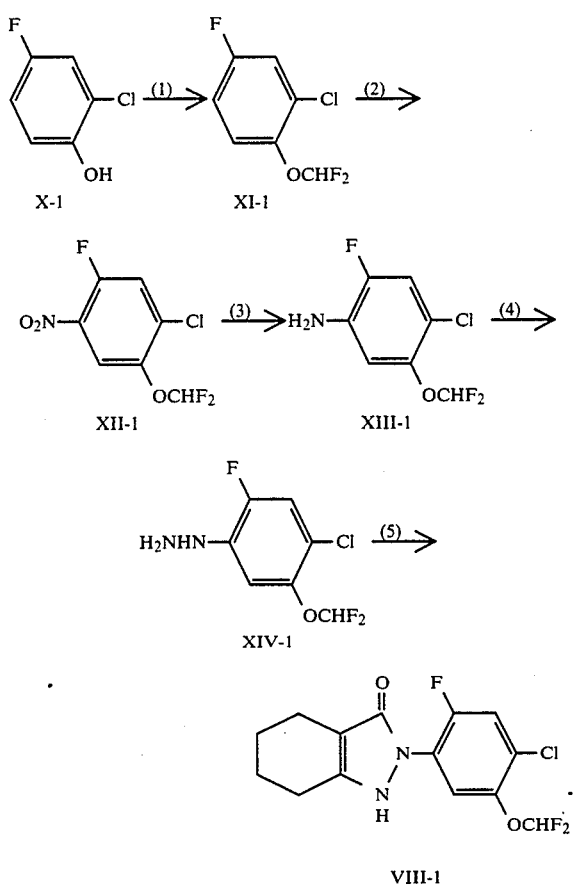

(1) 1-Chloro-2-difluoromethoxy-5-fluorobenzene XI-1

A mixture of 25 g of 2-chloro-4-fluorophenol X -1, 250 ml of isopropanol, 50 ml of water and 27 g of sodium hydroxide was stirred at 50°–60° C. Difluoromethane gas was introduced into the reaction mixture under stirring for 6 hours. During this period, each 25 g of sodium hydroxide was added 5 times by every one hour. After cooling, the reaction mixture was neutralized with 4N hydrochloric acid and shaken with ether. The ether layer was washed with saturated brine, dried and concentrated. The residue was purified by distillation to give 19.3 g of the titled compound XI -1 as a distillate boiling at 42°–43° C./5 mmHg.

NMR (CDCl$_3$) δ (TMS as internal standard) 6.47(1H, t, J=73 Hz), 6.77–7.36(3H, m).

(2) 4-Chloro-5-difluoromethoxy-2-fluoronitrobenzene XII -1

To 21 g of conc. nitric acid was dropwise added 28 g of conc. sulfuric acid at 0° C., and the mixture was heated at 60° C. At intervals of 3 minutes, 10 g of 1-chloro-2-difluoromethoxy-5-fluorobenzene was added in 5 portions to the mixture, which was kept at 60° C. for half an hour. After cooling, the reaction mixture was poured on ice water and shaken with chloroform. The chloroform layer was washed with water, dried and concentrated. The residue was chromatographed on a column of silica gel, eluting with n-hexane-ethyl acetate (100:15 v/v). The eluate was concentrated to give 11 g of the titled compound XII-1.

NMR (CDCl$_3$) δ (TMS as internal standard) 6.59(1H, t, J=72 Hz), 7.43(1H, d, J=10 Hz), 7.99(1H, d, J=7 Hz).

(3) 4-Chloro-5-difluoromethoxy-2-fluoroaniline XIII-1

To 5 g of 4-chloro-5-difluoromethoxy-2-fluoronitrobenzene XII-1 were added 10.4 ml of ethanol and 20.7 ml of hydrochloric acid, and the resultant mixture was stirred at room temperature. A solution of 14 g of stannous chloride dihydrate in 20.7 ml of ethanol was dropwise added in 10 minutes to the mixture, which was stirred for 20 hours. The reaction mixture was basified with 10% aqueous sodium hydroxide and shaken with chloroform. The chloroform layer was dried and concentrated. The residue was chromatographed on a column of silica gel, eluting with n-hexane-ethyl acetate (100:15 v/v). The eluate was concentrated to give 3.8 g of the titled compound XIII-1.

NMR (CDCl$_3$) δ (TMS as internal standard) 3.80(2H, brs), 6.37(1H, t, J=73 Hz), 6.60(1H, d, J=8 Hz), 6.98(1H, d, J=10 Hz).

XIII-1 was similarly prepared by using 10% palladium-carbon as a catalyst in ethyl acetate.

(4) 4-Chloro-5-difluoromethoxy-2-fluorophenylhydrazine XIV-1

A mixture of 13.3 g of 4-chloro-2-fluoro-5-difluoromethoxyaniline XIII-1 and 106 ml of hydrochloric acid was stirred at 0° C. A solution of 4.76 g of sodium nitrite in 35.4 ml of water was dropwise added in 10 minutes to the mixture, which was stirred at 0° to 5° C. for an hour. A solution of 35.4 g of stannous chloride dihydrate in 35.4 ml of hydrochloric acid was dropwise added in 15 minutes to the mixture, which was stirred at 0° to 5° C. for 2 hours. The reaction mixture was basified with 10% aqueous sodium hydroxide and shaken with chloroform. The chloroform layer was dried and concentrated, and 12.7 g of the titled compound XIV-1 thus obtained was used for the subsequent reaction without purification.

NMR (CDCl$_3$) δ (TMS as internal standard) 3.60(2H, brs), 5,40(1H, brs), 6.45(1H, t, J=73 Hz), 6.98(1H, d, J=10 Hz), 7.04(1H, d, J=7 Hz).

(5) 2-(4-Chloro-5-difluoromethoxy-2-fluorophenyl)-1,2,4,5,6,7-hexahydro-3H-indazol-3-one VIII-1

To 12.7 g of 4-chloro-5-difluoromethoxy-2-fluorophenylhydrazine were added 127 ml of toluene and 9.5 g of 2-ethoxycarbonylcyclohexanone V-1, and the resultant mixture was refluxed for 24 hours. After cooling, the reaction mixture was mixed with water and shaken with chloroform. The chloroform layer was dried and concentrated. The residue was chromatographed on a column of silica gel, eluting with n-hexane-ethyl acetate (1:1 v/v). The elutate was concentrated to give 6,0 g of the titled compound VIII-1 (containing a certain amount of its tautomer 2,3a,4,5,6,7-hexahydro compound).

REFERENCE EXAMPLE 3

4-Chloro-5-difluoromethoxy-2-fluoronitrobenzene XII-1

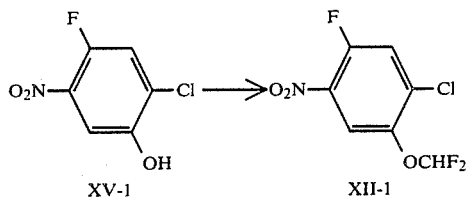

To 0.53 g of 2-chloro-4-fluoro-5-nitrophenol XV-1 were added 3 ml of isopropanol, 3 ml of water and 0.72 g of sodium hydroxide, and the resultant mixture was heated at 50° to 60° C. while introducing chlorodifluoromethane gas for 4 hours. The mixture was stirred for 4 hours and during that period mixed twice with 0.50 g of sodium hydroxide at intervals of 1.5 hours. After cooling, the reaction mixture was neutralized with 2N hydrochloride acid and shaken with dichloromethane. The dichloromethane layer was dried and concentrated. The residue was chromatographed on a column of silica gel, eluting with n-hexane-ethylacetate (100:5 v/v). The eluate was concentrated to give 0.24 g of the titled compound XII-1.

$n_D^{25.2}$ 1.5132.

Some examples of the herbicidal formulation of the present invention will be shown below, wherein the expression "part" means "part by weight".

FORMULATION 1

Fifty parts of Compound I-1. 2 parts of calcium ligninsulfonate, 3 parts of sodium lauryl sulfate, 5 part of white carbon and 40 parts of clay were admixed and pulverized to give a wettable powder.

FORMULATION 2

Ten parts of Compound I-1, 14 parts of polyoxyethylenestyryl phenyl ether, 6 parts of calcium dodecylbenzenesulfonate, 40 parts of xylene and 30 parts of cyclohexanone were well admixed and dissolved to give an emulsion.

FORMULATION 3

Two parts of Compound I-1, 2 parts of polyoxyethylene alkyl sulfate, 2 parts of calcium ligninsulfonate, 30 parts of bentonite and 64 parts of kaolin clay were admixed, pulverized, mixed with water, well kneaded and granulated. The resultant granules were dried to give granules.

FORMULATION 4

A mixture of 25 parts of Compound I-1, 3 parts of polyoxyethylene sorbitan monooleate, 3 parts of CMC and 69 parts of water was pulverized in the wet form until the particle size of the effective ingredient became below 5μ. Thus a suspension was obtained.

The compounds (I) of the present invention show excellent herbicidal effect against monocotyledonous and dicotyledonous weeds, for examples, Gramineous weeds such as barnyardgrass (*Echinochloa oryzicola*), broad-leaved weeds such as *Monochoria vaginalis* (Monochoria), *Vandellia angustifolia* (Vandelia), *Rotala indica* (Toothcup) or *Saggittoria pygmaea* (Arrowhead), or Cyperaceous weeds such as *Cyperus difformis* (Umbrella plant), *Scirpus juncoides* (Bulrush), *Eleocharis acicularis* (Slender soikerush), *Eleocharis kuroguwai* (Water chestnut), or *Cyperus serotinus* on paddy weeds, and against *Digitaria ciliaris* (large crabgrass) or *Amaranthus viridis* (slender amaranth) on upland weeds.

At an application rate of 1–40 g/are, the compounds (I) are nontoxic to common field crops such as corn, sugar cane, sorghum, rice, wheat, barley, soybean, peanut, and cotton; or a phytotoxicity in the crops, if any, is so slight that they could easily recover from the damage. Therefore, the compounds (I) can be applied as selective or non-selective herbicides to crop lands, e.g., upland fields, paddy fields, orchards, tea plantations, mulberry fluids, fallow lands, and pastures; or non-crop lands, e.g., railbeds, roads, lawns, factory sites, dry riverbeds, residential quarters, park green districts, forest lands, prepared lands, and vacant lands.

Furthermore, the compounds (I) are harmless to human beings, domestic animals, and birds or poultry, and show an extremely low toxicity to fish. Consequently, the herbicides comprising the compounds (I) are safe and present no problem of residual toxicity.

How to apply the compounds (I) as herbicides should be decided in consideration of the application purpose, objective plants, and application time. In general the compounds (I) can be applied in soil or over leaves.

The application concentration should also be decided in consideration of the application purpose, objective plants, and application time. Generally the concentration is about 1–5000 ppm.

The compounds (I) can be mixed with various carriers and formulated as powder, granules, wettable powder, emulsion, and the like. The carriers may be solid or liquid carriers, or a mixture of both.

The solid carriers include clay, talc, diatomaceous earth, bentonite, etc. The liquid carriers are exemplified by water, alkanols, acetone, benzene, toluene, xylene, solvent naphtha, cyclohexane, etc.

The formulatively acceptable emulsifiers, stabilizers, dispersants, suspending agents, spreaders, penetrants, or wetting agents may be added to the herbicidal composition comprising the compounds (I).

The compounds (I) may be used in combination with other herbicides, for example diuron, MCP, CNP, IPC, asulum, alachlor, trifluralin, and the like and they can be used together with insecticides, fungicides, fertilizers, pesticides for soil treatment in order to extend the herbicidal spectrum and to get additive or potentiative herbicidal actions.

The herbicides of this invention can be applied over clay loam as well as the ordinary soil such as sandy loam soil, loam soil, and the like. They can be applied even to the soil (e.g., sandy loam soil) which tends to have an influence on the occurrence of the herbicidal activity.

The effect of this invention will be confirmed by the following experiments.

EXPERIMENT 1

Herbicidal activity in paddy conditions (1) Pre-emergence Test:

| Mark(s) | Degree of the damage |
| --- | --- |
| 5 | complete death |
| 4 | severe |
| 3 | moderate |
| 2 | mild |
| 1 | slight |
| 0 | none |

Results of the test are summarized in Table 1.

TABLE 1

| Compd. Cord | Appln. Rate (g/are) | Chem. Injury | Barnyard-grass | Umbrella plant | *Monochoria vaginalis* | *Vandellia angustifolia* | Tooth-cup | Slender spikerush | Water chestnut | *Cyperus serotinus* | Arrow-head | Bul-rush |
| --- | --- | --- | --- | --- | --- | --- | --- | --- | --- | --- | --- | --- |
| A | 20 | 0 | 5 | 5 | 5 | 5 | 5 | 4–5 | 5 | 4–5 | 5 | 5 |
|   | 10 | 0 | 5 | 5 | 5 | 5 | 5 | 4–5 | 5 | 4–5 | 4 | 5 |
|   | 5.0 | 0 | 5 | 5 | 5 | 5 | 5 | 4–5 | 5 | 4–5 | 4 | 5 |
|   | 2.5 | 0 | 5 | 5 | 5 | 5 | 5 | 4–5 | 5 | 4 | 4 | 5 |
| B | 20 | 3 | 5 | 5 | 5 | 5 | 5 |   |   |   |   |   |
|   | 10 | 3 | 5 | 5 | 5 | 5 | 5 |   |   |   |   |   |
|   | 5 | 3 | 5 | 5 | 5 | 5 | 5 |   |   |   |   |   |
|   | 2.5 | 2 | 5 | 5 | 5 | 5 | 5 |   |   |   |   |   |
| C | 20 | 3 | 5 | 5 | 5 | 5 | 5 |   |   |   |   |   |
|   | 10 | 3 | 5 | 5 | 5 | 5 | 5 |   |   |   |   |   |
|   | 5 | 2 | 5 | 5 | 5 | 5 | 5 |   |   |   |   |   |
|   | 2.5 | 1 | 5 | 5 | 5 | 5 | 5 |   |   |   |   |   |
| D | 20 | 3 | 5 | 5 | 5 | 5 | 5 | 4–5 | 5 | 5 | 4–5 | 5 |
|   | 10 | 3 | 5 | 5 | 5 | 5 | 5 | 4–5 | 5 | 5 | 4 | 5 |
|   | 5 | 2 | 5 | 5 | 5 | 5 | 5 | 4–5 | 5 | 5 | 4 | 5 |
|   | 2.5 | 1 | 5 | 5 | 5 | 5 | 5 | 4–5 | 5 | 5 | 4 | 5 |

The paddy field soil (sandy clay loam) was charged in Wagner pot (1/10,000 are) and filled with water to make paddy water conditions. Rice seedlings (var. Nihonbare) in 2.5 leaf stage were transplanted. Seeds of test weeds, barnyardgrass, unbrella plant, *Monochoria vaginalis*, *Vandellia angustifolie*, toothcup and bulrush were sowed, and tubers of slender spikrush, water chestnut, *Cyperus difformis*, and arrowhead were planted in 5 mm depth.

Seven days after the transplantation of rice seedlings (2 days after the sowing of weed seeds and the planting of the tuber of weeds; pre-emergence stage), a suspension of a predetermined amount of the test compound in 5 ml/pot of water was applied directly to the paddy water with a pippet. After the treatment, the test plants were allowed to grow in a greenhouse for 20 days. Herbicidal effect and chemical injury of the test compound were examined.

| Compound | Test Compound Chemical Name | Note |
| --- | --- | --- |
| A | 3-chloro-2-(2,4-dichloro-5-difluoromethoxyphenyl)-4,5,6,7-tetrahydro-2H—indazole | Compd. I-1 |
| B | 3-chloro-2-(2,4-dichloro-5-methoxyphenyl)-4,5,6,7-tetrahydro-2H—indazole | EP Pat. 105,721 |
| C | 3-chloro-2-[2,4-dichloro-5-(1-methylethoxy)pheyl]-4,5,6,7-tetrahydro-2H—indazole | EP Pat. 105,721 |
| D | Oxadiazon | Control |

Evaluaton Method

Herbicidal effect and chemical injury were observed and appraised by the following evaluation standards.

(2) Post-emergence Test:

The paddy field soil (sandy clay loam) was changed in Wagner pot (1/10,000 are) and filled with water to make paddy field conditions. Rice seedlings (var. Nihonbare) in 2.5 leaf stage were transplanted. Seeds of test weeds, namely barnyardgrass, umbrella plant, *Monochoria vaginalis*, *Vandellia angustifoila* and toothcup were sowed.

Fourteen days after the transplanting of rice seedlings (8 days after the sowing of weed seeds; post emergence stage), a suspension of a prescribed amount of the test compound in 5 ml/pot of water was directly applied to the paddy water with a pippet. After the treatment, the test plants were allowed to grow in a greenhouse for 20 days. Herbicidal effect and chemical injury of the test compound were examined.

| Compound cord | Test Compound Chemical Name | Note |
| --- | --- | --- |
| A | 3-chloro-2-(2,4-dichloro-5-difluoromethoxyphenyl)-4,5,6,7-tetrahydro-2H—indazole | Cmpd. I-1 |
| B | 3-chloro-2-(2,4-dichloro-5-methoxyphenyl)-4,5,6,7-tetrahydro-2H—indazole | EP Pat. 105,721 |
| C | 3-chloro-2-[2,4-dichloro-5-(1-methylethoxy phenyl]-4,5,6,7-tetrahydro-2H—indazole | EP Pat. 105,721 |
| E | Benthiocarb | Control |

Evaluation Method

Herbicidal effect and chemical injury were observed and appraised by the following evaluation standards.

| Mark(s) | Degree of the damage |
|---------|---------------------|
| 5 | complete death |
| 4 | severe |
| 3 | moderate |
| 2 | mild |
| 1 | slight |
| 0 | none |

Results of the test are summarized in Table 2.

TABLE 2

Post-emergence Test

| Compd. Cord | Appln. Rate (g/are) | Chem. Injury Rice plant | Herbicidal Effect | | | | |
|---|---|---|---|---|---|---|---|
| | | | Barnyard-grass | Umbrella plant | *Monochoria vaginalis* | *Vandellia angustifolia* | Toothcup |
| A | 20 | 0 | 5 | 4 | 5 | 5 | 3 |
|   | 10 | 0 | 5 | 4 | 5 | 5 | 3 |
|   | 5  | 0 | 5 | 4 | 5 | 5 | 3 |
|   | 2.5| 0 | 4 | 3 | 4 | 5 | 3 |
| B | 20 | 3 | 5 | 5 | 5 | 5 | 4 |
|   | 10 | 3 | 5 | 5 | 5 | 5 | 4 |
|   | 5  | 3 | 5 | 5 | 5 | 5 | 3 |
|   | 2.5| 2 | 5 | 5 | 5 | 5 | 1 |
| C | 20 | 3 | 5 | 5 | 5 | 5 | 5 |
|   | 10 | 3 | 5 | 5 | 5 | 5 | 4 |
|   | 5  | 3 | 5 | 5 | 5 | 5 | 4 |
|   | 2.5| 2 | 5 | 5 | 5 | 5 | 4 |
| D | 30 | 0 | 5 | 4 | 4 | 4 | 4 |
|   | 15 | 0 | 4 | 2 | 2 | 2 | 2 |
|   | 7.5| 0 | 4 | 1 | 1 | 1 | 1 |
|   | 3.75| 0| 4 | 1 | 0 | 0 | 1 |

EXPERIMENT 2

Herbicidal Test in upland field

Pre-emergence Test:

Seeds of each test plant (20 seeds of weeds: large crabgrass, barnyardgrass, pale smartweed and slender amaranth, *Amaranthus viridis;* and 5 to 10 seeds of crops: corn, wheat, soybean, and cotton) were sowed on the loam charged in a square pot (10×10 cm, 10 cm in depth) made of polyvinyl chloride. After sowing, the seeds of the weeds were covered with the loam 5 mm in height and the seeds of the crops were covered with the loam 1 cm in height. A predetermined amount of the compound of the present invention was diluted with water at a rate of 10 L/are and applied uniformly over the surface of the loam with an automatic hand sprayer. Tween 20 (Nakarai Chemical Co.) was used at a concentration of 100 ppm as a spreader.

The pots were kept at 25° C. in a greenhouse. The herbicidal activity against each weed and the damage to the crops were evaluated 4 weeks after the application.

| Compd. Cord | Test Compound Chemical Name | Note |
|---|---|---|
| A | 3-chloro-2-(2,4-dichloro-5-difluoromethoxyphenyl)-4,5,6-7-tetrahydro-2H—indazole | Compd. I-1 |
| B | 3-chloro-2-(2,4-dichloro-5-methoxyphenyl)-4,5,6,7-tetra-hydro-2H—indazole | EP Pat. 105,721 |
| C | 3-chloro-2-[2,4-dichloro-5-(1-methylethoxy)phenyl]-4,5,6,7-tetrahydro-2H—indazole | EP Pat. 105,721 |
| F | Linuron | Control |

Evaluation Method

Herbicidal effect and chemical injury were observed and appraised by the following evaluation standards.

| Mark(s) | Degree of the damage |
|---------|---------------------|
| 5 | complete death |
| 4 | severe |
| 3 | moderate |
| 2 | mild |
| 1 | slight |
| 0 | none |

Results of the test are summarized in Table 3.

TABLE 3

| Compd. Cord | Appln. Rate (g/are) | Pre-emergence Test | | | | | | | |
|---|---|---|---|---|---|---|---|---|---|
| | | Herbicidal Effect | | | | Chemical Injury | | | |
| | | Large crabgrass | Barnyard grass | Pale smartweed | Slender amaranth | Corn | Wheat | Soybean | Cotton |
| A | 20  | 5 | 3 | 5 | 4 | 2 | 0 | 0 | 0 |
|   | 10  | 5 | 3 | 4 | 5 | 1 | 0 | 0 | 0 |
|   | 5   | 4 | 2 | 3 | 5 | 0 | 0 | 0 | 0 |
|   | 2.5 | 4 | 1 | 3 | 4 | 0 | 0 | 0 | 0 |
| B | 20  | 5 | 4 | 4 | 5 | 1 | 0 | 1 | 0 |
|   | 10  | 5 | 4 | 4 | 5 | 0 | 0 | 1 | 0 |
|   | 5   | 5 | 2 | 3 | 5 | 0 | 0 | 1 | 0 |
|   | 2.5 | 5 | 2 | 2 | 4 | 0 | 0 | 1 | 0 |

TABLE 3-continued

| Compd. Cord | Appln. Rate (g/are) | Pre-emergence Test Herbicidal Effect | | | | Chemical Injury | | | |
|---|---|---|---|---|---|---|---|---|---|
| | | Large crabgrass | Barnyard grass | Pale smartweed | Slender amaranth | Corn | Wheat | Soybean | Cotton |
| C | 20 | 5 | 5 | 5 | 5 | 2 | 0 | 1 | 0 |
|   | 10 | 5 | 5 | 5 | 5 | 0 | 0 | 1 | 0 |
|   | 5  | 5 | 3 | 5 | 5 | 0 | 0 | 0 | 0 |
|   | 2.5| 5 | 3 | 4 | 4 | 0 | 0 | 0 | 0 |
| F | 20 | 5 | 5 | 5 | 5 | 0 | 4 | 1 | 0 |
|   | 10 | 5 | 5 | 5 | 5 | 0 | 1 | 0 | 0 |
|   | 5  | 5 | 5 | 5 | 5 | 0 | 0 | 0 | 0 |
|   | 2.5| 0 | 0 | 0 | 5 | 0 | 0 | 0 | 0 |

EXPERIMENT 3

The same herbicidal test (1) Pre-emergence test as in Experiment 1 was performed on Compound I-2. As the result, complete herbicidal effect was observed at an application rate of 0.04 g/are against barnyardgrass, umbrella plant, *Monochoria vaginalis, Vandellia angustifolia* and toothcup without chemical injury in rice plant.

Accordingly the compounds of the present invention are very useful as herbicides, showing excellent herbicidal effects against weeds with no or negligibly low chemical injury in crop plants.

What we claim is:

1. A compound of the formula:

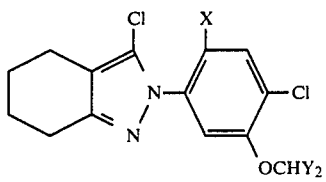

wherein X and Y each is halogen or a phytologically acceptable acid addition salt thereof.

2. A compound according to claim 1, namely 3-chloro-2-(2,4-dichloro-5-difluoromethoxyphenyl)-4,5,6,7-tetrahydro-2H-indazole.

3. A compound according to claim 1, namely 3-chloro-2-(4-chloro-5-difluoromethoxy-2-fluorophenyl)-4,5,6,7-tetrahydro-2H-indazole.

4. A herbicidal composition comprising a herbicidally effective amount of a compound or salt thereof according to claim 1 together with one or more carriers, diluents and/or excipients.

* * * * *